(12) United States Patent
Sun et al.

(10) Patent No.: US 11,253,270 B2
(45) Date of Patent: Feb. 22, 2022

(54) OSTEOTOMY DEVICE AND OPERATION METHOD THEREFOR

(71) Applicant: Suzhou Microport Orthorecon Co., LTD., Suzhou (CN)

(72) Inventors: Yandong Sun, Suzhou (CN); Fangqiu Hu, Suzhou (CN); Kaiyu Zhao, Suzhou (CN); You Wu, Suzhou (CN)

(73) Assignee: Suzhou Microport Orthorecon Co., LTD.

( * ) Notice: Subject to any disclaimer, the term of this patent is extended or adjusted under 35 U.S.C. 154(b) by 0 days.

(21) Appl. No.: 16/970,903

(22) PCT Filed: Mar. 6, 2019

(86) PCT No.: PCT/CN2019/077193
§ 371 (c)(1),
(2) Date: Aug. 18, 2020

(87) PCT Pub. No.: WO2019/184670
PCT Pub. Date: Oct. 3, 2019

(65) Prior Publication Data
US 2020/0383690 A1    Dec. 10, 2020

(30) Foreign Application Priority Data

Mar. 27, 2018  (CN) .......................... 201810257229.1

(51) Int. Cl.
*A61F 5/00*     (2006.01)
*A61B 17/15*    (2006.01)
*A61B 17/56*    (2006.01)

(52) U.S. Cl.
CPC .......... *A61B 17/155* (2013.01); *A61B 17/151* (2013.01); *A61B 17/56* (2013.01); *A61B 2017/564* (2013.01)

(58) Field of Classification Search
CPC combination set(s) only.
See application file for complete search history.

(56) References Cited

U.S. PATENT DOCUMENTS

2007/0233140 A1*  10/2007  Metzger .............. A61B 17/155
                                                         606/88
2011/0046629 A1    2/2011  Green, II et al.

FOREIGN PATENT DOCUMENTS

CN      103945779 A    7/2014
CN      104027153 A    9/2014
(Continued)

OTHER PUBLICATIONS

Japanese Office Action, dated Jul. 27, 2021, 4 pages.
(Continued)

*Primary Examiner* — Sameh R Boles
(74) *Attorney, Agent, or Firm* — Adsero IP

(57) ABSTRACT

Disclosed is an osteotomy device, comprising an osteotomy plate (10), a fixing plate (20) and an adjusting structure (30), wherein the osteotomy plate (10) is mounted on a femur (B) via the fixing plate (20), two ends of the adjusting structure (30) are respectively connected to the fixing plate (20) and the osteotomy plate (10), and the osteotomy plate (10) slides left and right relative to the fixing plate (20) via the adjusting structure (30); and the osteotomy plate (10) has a femoral osteotomy groove (11) for performing an osteotomy from four sides and a femoral trochlear osteotomy groove (12) for performing femoral trochlear osteotomy.

11 Claims, 4 Drawing Sheets

(56) References Cited

FOREIGN PATENT DOCUMENTS

| | | |
|---|---|---|
| CN | 105193475 A | 12/2015 |
| CN | 205019144 U | 2/2016 |
| CN | 107007319 A | 8/2017 |
| CN | 107049415 A | 8/2017 |
| CN | 206482630 U | 9/2017 |
| GB | 2441863 | 3/2008 |
| WO | WO-94-08528 | 4/1994 |
| WO | WO-2008-019114 A2 | 2/2008 |
| WO | WO-2019/184670 A1 | 10/2019 |

OTHER PUBLICATIONS

Extended European Search Report, Application No. 1977984.6, dated Sep. 24, 2021, 10 pages.
Translation of International Search Report, International Application No. PCT/CN2019/077193, dated May 31, 2019, 3 pages.
Chinese Office Action, CN Application No. 201810257229.1, dated Apr. 6, 2021, 7 pages.

* cited by examiner

OSTEOTOMY DEVICE AND OPERATION METHOD THEREFOR

CROSS REFERENCE TO RELATED APPLICATIONS

This application is a 371 National Phase of PCT/CN2019/077193 filed Mar. 6, 2019, by Yandong SUN et al. titled, "Osteotomy Device and Operation Method Therefor," which claims the benefit of Chinese Patent Application No. 201810257229.1, entitled "osteotomy device", filed on Mar. 27, 2018, the entire content of which is incorporated herein in its entirety.

TECHNICAL FIELD

The present disclosure relates to a technology field of medical devices, in particular, to an osteotomy device and a method for operating the osteotomy device.

BACKGROUND

In total knee arthroplasty, femoral osteotomy is an extremely important step. Since an inner surface of existing femoral prosthesis has four sides and protrudes inward at the middle portion where a femoral trochlear is located, a doctor needs to treat a femur into a specific shape corresponding to the prosthesis, so as to mount the femoral prosthesis. That is, a four-sided osteotomy is performed on a distal end surface of the femur (the surface connected to the prosthesis), and the distal end surface of the femur is formed to have a concave shape at the femoral trochlear. In this process, whether an osteotomy plate is firmly fixed, and whether the repeated disassembly and assembly of the osteotomy plate is accurate will directly affect the effect of the osteotomy.

At present, doctors generally need to use different osteotomy plates for four-sided osteotomy operation and femoral trochlear osteotomy operation when performing anterior and posterior femoral condyle treatment. This surgical procedure is complicated to operate, and repeated disassembly and assembly of the osteotomy plate is also very easy to reduce the accuracy of the osteotomy and increase the probability of operation errors. Moreover, the separate use of multiple sets of osteotomy plates not only increases the number of devices, but also increases the manufacturing cost. At the same time, it also increases the maintenance cost of disinfection and sterilization and repeated transportation during the use in hospital.

In addition, unlike the four-sided osteotomy, the position of the femoral trochlear osteotomy must correspond to the position of the femoral prosthesis trochlear track, so the fixing position of the femoral trochlear osteotomy plate is more stringent. However, the osteotomy plate currently used for the femoral trochlear osteotomy cannot be adjusted in a left-right direction after it is fixed, which also increases the difficulty for the doctor to determine the centering and positioning. Since the femoral trochlear is the track where a patella slides with respect to the femur, if the centering position of the femoral trochlear osteotomy is not accurate and the deviation in the left-right direction occurs, it will directly affect the position where the femoral prosthesis is mounted. It will further affect a deviation of a sliding track of the patella after the prosthesis is reset, which may cause abnormal patella track, anterior patella pain and other problems.

SUMMARY

According to various embodiments of the present disclosure, an osteotomy device and a method for operating the osteotomy device are provided.

According to one aspect of the present disclosure, an osteotomy device is provided, which includes an osteotomy plate, a fixing plate and an adjusting structure. The osteotomy plate is configured to be mounted on a femur via the fixing plate. Both ends of the adjusting structure are configured to be connected to the fixing plate and the osteotomy plate, respectively. The osteotomy plate is capable of sliding in a left-right direction with respect to the fixing plate via the adjusting structure. The osteotomy plate has femoral osteotomy grooves to perform a four-sided osteotomy and a femoral trochlear osteotomy groove to perform a femoral trochlear osteotomy.

In one of the embodiments, upper and lower ends of the fixing plate are each provided with a latching tooth. A surface of the osteotomy plate facing the fixing plate is provided with a sliding groove. The latching tooth is slidably engaged in the sliding groove. The latching tooth and the sliding groove are capable of sliding with respect to each other in a horizontal direction.

In one of the embodiments, the adjusting structure includes a rotary knob and an eccentric wheel. The rotary knob is connected to the eccentric wheel and rotatably connected to the osteotomy plate. The eccentric wheel connected to the fixing plate. When the rotary knob rotates, the eccentric wheel moves eccentrically with respect to the rotary knob, so as to enable the osteotomy plate to slide in the left-right direction with respect to the fixing plate.

In one of the embodiments, the eccentric wheel includes a rotary connecting portion and an eccentric portion. The rotary connecting portion is connected to the rotary knob. The eccentric portion is deviated from a rotation axis of the rotary knob.

In one of the embodiments, the fixing plate is provided with a groove, the eccentric portion is embedded in the groove. When the eccentric wheel rotates along with the rotary knob, the eccentric portion is capable of sliding in an up-down direction along the groove.

In one of the embodiments, the osteotomy plate is provided with a cavity penetrating through the osteotomy plate. The cavity and the groove are communicated to form a hollow cavity. The rotary knob is located in the cavity. When the rotary knob rotates, the rotary knob abuts against a sidewall of the cavity to drive the osteotomy plate to slide in the left-right direction.

In one of the embodiments, the eccentric wheel and the rotary knob are capable of moving in an axial direction with respect to each other. The eccentric wheel is radially restricted to the rotary knob. An elastic compression member is provided between the eccentric wheel and the rotary knob. Both ends of the elastic compression member elastically abut against the eccentric wheel and the rotary knob, respectively.

In one of the embodiments, the rotary knob has a stepped shape. One end of the rotary knob adjacent to the eccentric wheel has an inserting portion, and the other end thereof has a toothed disc. The rotary connecting portion of the eccentric wheel is provided with an inserting slot matching with the inserting portion. An end of the cavity away from the fixing plate has a toothed opening. The toothed disc is capable of being embedded in or removed from the toothed opening along the rotation axis of the rotary knob. When the toothed disc is embedded in the toothed opening, the toothed opening restricts a rotational movement of the rotary knob with respect to the osteotomy plate.

In one of the embodiments, a bottom portion of the groove is provided with a through hole penetrating through the fixing plate.

In one of the embodiments, an end of the cavity adjacent to the fixing plate has a restricting groove. When the eccentric wheel moves to a limiting position that is required for the adjusting structure to adjust a stroke of the osteotomy plate, the eccentric wheel abuts against an end of the restricting groove, such that the eccentric wheel is restricted from rotating eccentrically.

In one of the embodiments, a side of the fixing plate away from the osteotomy plate is provided with a fixing nail configured to mount the fixing plate on the femur.

In the osteotomy device, the osteotomy plate includes the femoral osteotomy grooves to perform the four-sided osteotomy and the femoral trochlear osteotomy groove to perform a femoral trochlear osteotomy, such that the femoral trochlear osteotomy operation can be performed after performing the four-sided osteotomy operation without replacing the osteotomy plate, which effectively reduces the number of devices, while avoiding repeated disassembly and assembly, and simplifying the operation steps. In addition, the osteotomy device can use the adjusting structure to conveniently adjust the sliding of the osteotomy plate in the left-right direction with respect to the fixing plate, so as to adjust the osteotomy plate to a position where the femoral trochlear osteotomy groove is directly opposite to the femoral trochlear, thereby improving the accuracy of the femoral trochlear osteotomy, avoiding that the incorrect corresponding position of the femoral trochlear osteotomy results in an abnormal sliding track of the patella after the prosthesis reset.

According to another aspect, in present disclosure, the side of the fixing plate away from the osteotomy plate is provided with a fixing nail. The fixing nail on the fixing plate can provide an initial fixing for the osteotomy plate, thus increasing the stability of the osteotomy plate during the process of adjusting the centering position of the osteotomy plate in the left-right direction by a doctor via the adjusting structure. After the centering is determined, the fixing nail cooperates with a driven oblique nail to completely fix the osteotomy plate, so as to ensure the stability during the osteotomy and the accuracy of the osteotomy.

According to another aspect of the present disclosure, a method for operating the aforementioned osteotomy device is provided. The method includes: fixing the osteotomy device on the femur via the fixing plate; adjusting the adjusting structure such that the osteotomy plate slides to an appropriate position in the left-right direction with respect to the fixing plate; performing the four-sided osteotomy along the femoral osteotomy grooves; and performing the femoral trochlear osteotomy along the femoral trochlear osteotomy groove.

BRIEF DESCRIPTION OF THE DRAWINGS

In order to more clearly explain the embodiments of the present disclosure or the technical solutions in the prior art, the drawings required in the embodiments or the description of the prior art will briefly be introduced below. Apparently, the drawings in the following description are only some embodiments of the present disclosure. For those of ordinary skill in the art, without paying any creative work, drawings of other embodiments can be obtained based on these drawings.

DETAILED DESCRIPTION OF THE EMBODIMENTS

In order to better understand the present disclosure, the present disclosure will be described more fully below with reference to related drawings. The drawings illustrate better implementations of the present disclosure. However, the present disclosure can be implemented in many different forms and is not limited to embodiments as described therein. Rather, providing these embodiments is to help a more thorough and comprehensive understanding of the disclosure of this disclosure.

Figure 5:
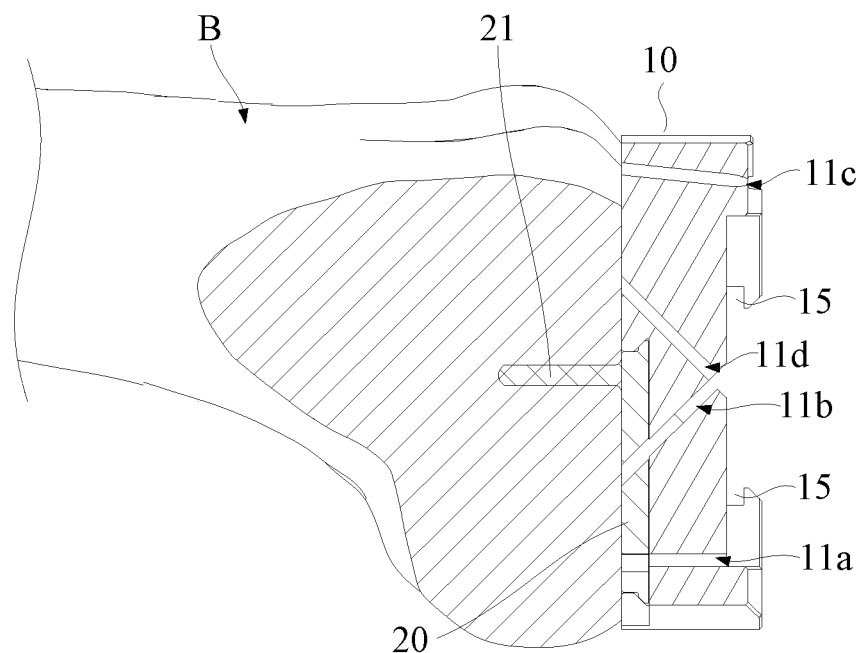
FIG. 5 is a cross-sectional view taken along a line A-A in FIG. 4.

In order to more clearly describe the structure of the above-mentioned device, the present disclosure defines the terms "distal end" and "proximal end". The above-mentioned terms are common terms in the field of medical devices. Specifically, "distal end" refers to an end away from the operator during a surgical, and "proximal end" refers to an end adjacent to the operator during the surgical. Taking FIG. 5 as an example, the right side of FIG. 5 is the distal end, and the left side thereof is the proximal end.

It should be noted that when an element is referred to as being "fixed on" another element, it may be directly on another element or there may also be an intermediate element therebetween. When an element is considered to be "connected" to another element, it may be directly connected to another element or there may be an intermediate element therebetween. The "connection" may include a detachable connection. As used herein, the terms "internal", "external", "left", "right", and similar expressions are for illustration only and are not meant to be the only embodiments.

Figure 1:
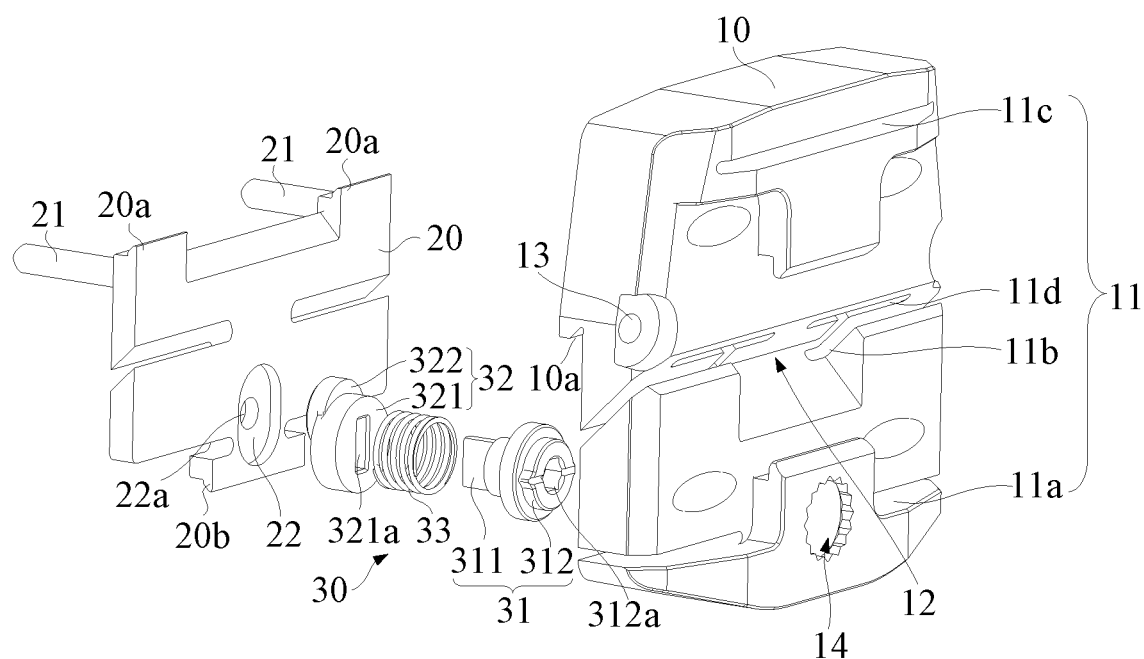
FIG. 1 is a structural explosive view of an osteotomy device according to an embodiment.
Figure 2:
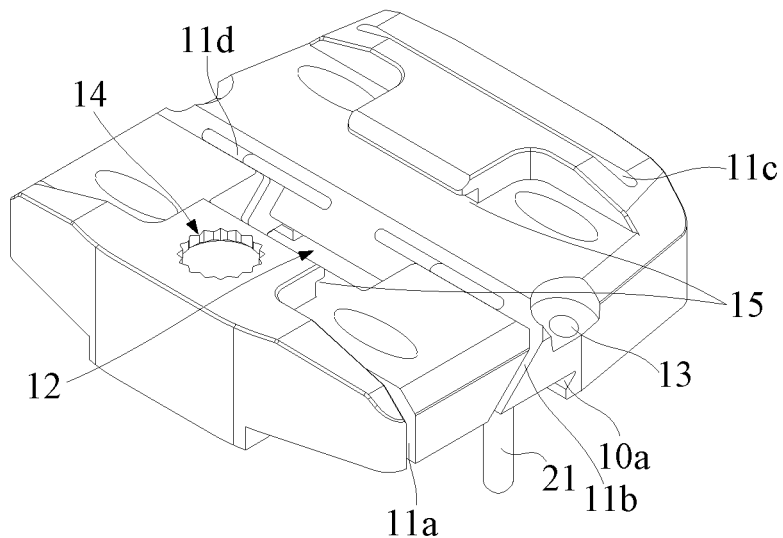
FIG. 2 is an assembly structure view of an osteotomy plate and a fixing plate of the osteotomy device shown in FIG. 1.

Referring to FIGS. 1 and 2, an osteotomy device according to an embodiment includes an osteotomy plate 10, a fixing plate 20, and an adjusting structure 30. The osteotomy plate 10 is mounted on a femur B via the fixing plate 20, and is movable in a left-right direction with respect to the fixing plate 20. That is, the osteotomy device may adjust a position of the osteotomy plate 10 in the left-right direction with respect to the femur B, so as to perform an osteotomy at an appropriate position. Herein, the position in the left-right direction is defined as below: referring to FIGS. 1 and 5, the osteotomy device is attached to a distal end face of the femur B. In a plane where the distal end face of the femur B is located, a direction parallel to an osteotomy groove 11a is the left-right direction, that is, a horizontal direction, and a direction perpendicular to the horizontal direction is an up-down direction, that is, a vertical direction.

In this embodiment, the osteotomy plate 10 has femoral osteotomy grooves 11 for performing a four-sided osteotomy, which, specifically, are femoral osteotomy grooves 11a, 11b, 11c, and 11d. The osteotomy plate 10 further has a femoral trochlear osteotomy groove 12 for performing a femoral trochlear osteotomy. The adjusting structure 30 is configured to drive the osteotomy plate 10 to slide in the left-right direction, so as to adjust a position of the osteotomy plate 10 with respect to the femur B, thus allowing an osteotomy tool such as a sawblade to perform the four-sided osteotomy along the femoral osteotomy grooves 11a, 11b, 11c, and 11d, respectively, while the femoral trochlear osteotomy groove 12 allows the osteotomy tool to perform the femoral trochlear osteotomy.

In the above embodiment, since the adjusting structure 30 can adjust the position of the osteotomy plate 10 with respect to the femur B, the osteotomy plate 10 can be adjusted to a position where the femoral trochlear osteotomy groove 12 is directly opposite to the femoral trochlear, so as to ensure that the position of the femoral trochlear osteotomy corresponds to a moving track of a prosthetic trochlear of the femur B, thereby avoiding that the incorrect corresponding position of the femoral trochlear osteotomy results in an abnormal sliding track of the patella after the prosthesis is reset. In addition, since the osteotomy device can be used to complete both of the four-sided osteotomy operation and the femoral trochlear osteotomy operation, that is, after the four-sided osteotomy operation is completed, the femoral trochlear osteotomy operation is continued without disassembling and replacing the osteotomy plate 10. As such, the operation is more accurate, the surgical time is reduced, the surgical efficiency is improved, and the case that a four-sided osteotomy plates 10 and a femoral trochlear osteotomy plate 10 are respectively required to perform the osteotomy in the conventional total knee arthroplasty is avoided, which effectively reduces the number of devices, simplifies the operation steps, and reduces the cost of surgical and maintenance.

It should be noted that, in some embodiments, the osteotomy plate 10 is of symmetrical structure, so as to fit the femur B to perform the osteotomy operation at the corresponding position. In this embodiment, the femoral trochlear osteotomy groove 12 is located at a middle portion of the osteotomy plate 10, such that when the osteotomy plate 10 is adjusted to a centering portion of the femur B, the femoral trochlear osteotomy groove 12 is directly opposite to the femoral trochlear. Such a configuration is convenient to rapidly adjust the movement of the osteotomy plate 10 in the left-right direction with respect to the femur B to the femoral trochlear osteotomy groove 12 and position the osteotomy plate 10 at the centering portion, so as to perform the osteotomy operation on the femoral trochlear, thereby increasing the adjusting efficiency, while avoiding the deviation of the position of the femoral trochlear osteotomy, improving the surgical effect.

Figure 3:
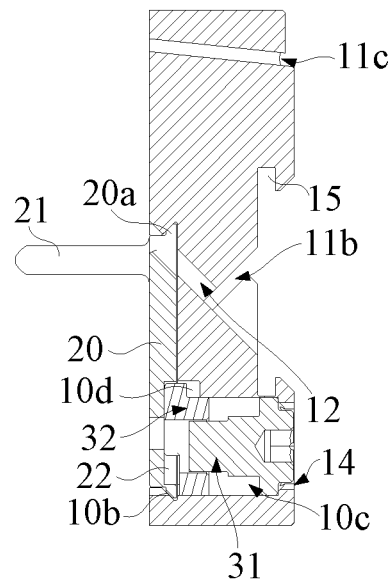
FIG. 3 is a cross-sectional view of the osteotomy device shown in FIG. 2.

The osteotomy plate 10 and the fixing plate 20 are each provided with a sliding connection structure on surfaces (i.e., the proximal end surface of the osteotomy plate 10 and the distal end surface of the fixing plate 10) thereof adjacent to each other, and the sliding connection structures are matched with each other. Referring to FIG. 3, in some embodiments, upper and lower ends of the fixing plate 20 are each provided with latching teeth 20a, 20b that extend in the horizontal direction. A surface of the osteotomy plate 10 facing the fixing plate 20 is provided with sliding grooves 10a, 10b that extend in the horizontal direction at a position corresponding to the latching teeth 20a, 20b. The latching tooth 20a is slidably engaged in the sliding groove 10a, and the latching tooth 20b is slidably engaged in the sliding groove 10b. In this embodiment, since the latching tooth 20a and the latching tooth 20b on the fixing plate 20 are engaged in the sliding groove 10a and the sliding groove 10b on the osteotomy plate 10 by means of sliding engagement, when the osteotomy plate 10 slides with respect to the fixing plate 20, the fixing plate 20 can well support the osteotomy plate 10 in the up-down direction, such that the osteotomy plate 10 has a better stability when sliding in the left-right direction with respect to the fixing plate 20, so as to ensure the accuracy of the position adjustment of the osteotomy. In this embodiment, the latching tooth 20a may be a continuous latching tooth, or may be composed of two or more discontinuous latching tooth (as shown in FIG. 3). In the latter case, the latching tooth 20a, as well as 20b, may also be composed of two or more posts. In some other embodiments, the upper and lower ends of the fixing plate 20 may be each provided with the sliding groove, and the surface of the osteotomy plate 10 facing the fixing plate 20 is provided with the latching tooth that is engaged in the sliding groove. The sliding groove and the latching tooth may also be replaced with other sliding connection structure, as long as the relative horizontal sliding between the osteotomy plate 10 and the fixing plate 20 can be achieved. For example, the joint surfaces of the fixing plate 20 and the osteotomy plate 10 are each provided with a slider and a sliding groove that are in a sliding engagement, such that when the slider slides along the sliding groove, the osteotomy plate 10 can also slide with respect to the fixing plate 20, so that when the osteotomy plate 10 is mounted on the femur B via the fixing plate 20, a relative position of the osteotomy plate 10 to the femur B can be adjusted in a sliding way to meet the needs of osteotomy, and the redundant description thereof will not be made herein.

In some embodiments, a side of the fixing plate 20 away from the osteotomy plate 10 is provided with fixing nails 21. The fixing nails 21 can be used to pre-fix the osteotomy device.

It should be noted that, the number of the fixing nails 21 is not limited hereto. In this embedment, the number of the fixing nails 21 is two. The two fixing nails 21 are symmetrically arranged on the fixing plate 20 in the left-right direction. The fixing nail 21 may be a column-shaped spike, which is convenient to be driven into the femur B, while having better stability. In addition, nail holes 13 are inclinedly provided on both sides of the osteotomy plate 10, such that after adjusting the relative position of the osteotomy plate 10 and the femur B via the adjusting structure 30, fasteners such as nails extending through the nail holes 13 can be driven into the femur B to position the osteotomy device, so as to ensure the stability during the osteotomy operation and improve the accuracy of the osteotomy.

The osteotomy plate 10 is adaptively provided with a hollow portion to reduce weight. The shape, number and position of the hollow portion are not limited hereto. A plurality of hollow portions can be provided without affecting the strength of the osteotomy plate 10 and the osteotomy operation. In some other embodiments, an even number of hollow portions can be provided symmetrically on the osteotomy plate 10. Referring to FIG. 2, in this embodiment, a side of the osteotomy plate 10 away from the fixing plate 20 is provided with a T-shaped groove 15, such that after the osteotomy operation, the osteotomy plate 10 can be taken out by a tool matching with the T-shaped groove 15, such as a sliding hammer.

Referring to FIG. 1 again, the adjusting structure 30 includes a rotary knob 31 and an eccentric wheel 32. The rotary knob 31 is connected to the eccentric wheel 32, and is rotatably connected to the osteotomy plate 10. The eccentric wheel 32 is connected to the fixing plate 20. When the rotary knob 31 rotates, the eccentric wheel 32 moves eccentrically with respect to the rotary knob 31, so as to enable the osteotomy plate 10 to slide in the left-right direction with respect to the fixing plate 20.

The eccentric wheel 32 includes a rotary connecting portion 321 and an eccentric portion 322. The rotary connecting portion 321 is connected to the rotary knob 31. The eccentric portion 322 is deviated from a rotation axis of the rotary knob 31. In this embodiment, the fixing plate 20 is provided with a groove 22, and the eccentric portion 322 is embedded in the groove 22. When the eccentric wheel 32 rotates along with the rotary knob 31, since the restriction of the mutual engagement between the latching tooth 20*a* and the latching tooth 20*b* and the sliding groove 10*a* and the sliding groove 10*b*, the fixing plate 20 and the osteotomy plate 10 will not be displaced in the up-down direction with respect to each other, while the eccentric portion 322 slides in the up-down direction along the groove 22. Therefore, when the eccentric wheel 32 moves eccentrically, the changes of the displacement in the up-down direction does not interfere with the fixing plate 20. It should be understood that, the groove 22 may be an elongated groove or a kidney groove with an upward and downward extending tendency.

The extending direction of the groove 22 is perpendicular to the sliding direction of the osteotomy plate 10 with respect to the fixing plate 20, such that when the eccentric portion 322 moves with the rotary knob 31, the force between the eccentric portion 322 and the fixing plate 20 is in the left-right direction, which makes a good sliding effect in the left and right direction between the osteotomy plate 10 and the fixing plate 20.

As shown in FIG. 3, the osteotomy plate 10 is provided with a cavity 10*c* penetrating through the osteotomy plate 10. When the fixing plate 20 is engaged with the osteotomy plate 10, the cavity 10*c* corresponds to the position of the groove 22. That is, the cavity 10*c* and the groove 22 are communicated to form a hollow cavity for accommodating the adjusting structure 30. The rotary knob 31 is located in the cavity 10*c*. When the rotary knob 31 rotates, since the eccentric wheel 32 moves eccentrically with respect to the rotary knob 31, the interaction force of the eccentric wheel 32 posed on the rotary knob 31 will enable the rotary knob 31 to abut against a sidewall of the cavity 10*c*, so as to drive the osteotomy plate 10 to slide in the left-right direction with respect to the fixing plate 20 along the sliding groove 10*a* and the sliding groove 10*b*.

The eccentric wheel 32 and the rotary knob 31 can move relatively in an axial direction, and the eccentric wheel 32 is restricted to the rotary knob 31 in a radial direction. An elastic compression member 33 is provided between the eccentric wheel 32 and the rotary knob 31. Both ends of the elastic compression member 33 elastically abut against the eccentric wheel 32 and the rotary knob 31, respectively. The axial direction and the radial direction used herein are defined as blow: referring to FIG. 5, the osteotomy device is attached to the distal end surface (osteotomy surface) of the femur B, and a direction perpendicular to the osteotomy surface (that is, a direction parallel to the rotation axis of the rotary knob 31) is the axial direction, a direction perpendicular to the axial direction is the radial direction. The elastic compression member 33 herein may be a compression spring, or may be an elastic ring with better contraction capability.

In this embodiment, since the eccentric wheel 32 and the rotary knob 31 can move relatively in the axial direction, ends of the eccentric wheel 32 and the rotary knob 31 away from the elastic compression member 33 can be respectively pressed to compress the elastic compression member 33, so as to change an axial distance between the eccentric wheel 32 and the rotary knob 31, thereby avoiding that the eccentric wheel 32 interferes the fixed plate 20 when assembling the fixing plate 20 and the osteotomy plate 10. In addition, after the fixing plate 20 and the osteotomy plate 10 are assembled, since both ends of the elastic compression member 33 elastically abut against the eccentric wheel 32 and the rotary knob 31, respectively, the eccentric wheel 32 abuts against the groove 22, subjected to the elastic compression member 33. Since the eccentric wheel 32 is restricted to the rotary knob 31 in the radial direction, when the rotary knob 31 rotates, the eccentric wheel 32 will rotate along with the rotary knob 31, so as to enable the osteotomy plate 10 to slide in the left-right direction with respect to the fixing plate 20, and adjust the left-right position of the osteotomy plate 10 with respect to the femur B, so as to perform the osteotomy operation in an appropriate position.

A bottom portion of the groove 22 may be provided with a through hole 22*a* penetrating through the fixing plate 20. As such, pressing the eccentric wheel 32 via the through hole 22*a* will enable the eccentric wheel 32 to compress the elastic compression member 33 to be away from the fixing plate 20, and finally move the eccentric portion 322 of the eccentric wheel 32 out of the groove 22. At this time, the fixing plate 20 is not constrained by the eccentric wheel 32 in the left-right direction, such that the fixing plate 20 and the osteotomy plate 10 can slide away from each other along the sliding groove 10*a* and the sliding groove 10*b*.

The rotary knob 31 may have a stepped shape. One end of the rotary knob 31 adjacent to the eccentric wheel 32 has an inserting portion 311, and the other end thereof has a toothed disc 312. The rotary connecting portion 321 of the eccentric wheel 32 is provided with an inserting slot 321*a* matching with the inserting portion 311. It can be understood that the cross-sectional shapes of the inserting slot 321*a* and the inserting portion 311 may be non-circular, such as rectangular, rounded rectangle, etc., so as to ensure the radial restriction between the eccentric wheel 32 and the rotary knob 31, while the eccentric wheel 32 and the rotary knob 31 can move relatively in the axial direction.

In this embodiment, an end of the cavity 10*c* away from the fixing plate 20 has a toothed opening 14. The toothed disc 312 can be embedded in or removed from the toothed opening 14 along the rotation axis of the rotary knob 31. When the toothed disc 312 is embedded in the toothed opening 14, the toothed opening 14 restricts the rotational movement of the rotary knob 31 with respect to the osteotomy plate 10, so as to lock the relative position of the osteotomy plate 10 and the fixing plate 20, thereby avoiding a displacement between the osteotomy plate 10 and the fixing plate 20 during operation errors or mounting the osteotomy device.

It should be noted that, in the above embodiments, when the rotary knob 31 compresses the elastic compression member 33, the toothed disc 312 will move out of the toothed opening 14 as the rotary knob 31 moves toward the fixing plate 20, so as to disengage the toothed disc 312 from the toothed opening 14, such that the rotary knob 31 can rotate with respect to the osteotomy plate 10, thereby adjusting the relative position between the osteotomy plate 10 and the fixing plate 20 in the horizontal direction. In this way, the femoral trochlear osteotomy groove 12 on the osteotomy plate 10 is aligned with the femoral trochlear for the osteotomy operation.

An end surface of the toothed disc 312 is provided with an operating portion 321*a*, so as to rotate the rotary knob 31 with a tool that cooperates with the operating portion 321*a*.

The operating portion 321a may be a hexagonal counterbore. Correspondingly, the rotary knob 31 can be rotated by a tool such as a wrench or a screwdriver matched with the hexagonal counterbore, so as to drive the osteotomy plate 10 to slide in the left-right direction with respect to the fixing plate 20 via the eccentric movement of the eccentric wheel 32, and adjust the positions of the osteotomy plate 10 in the left-right direction with respect to the femur B, such that the femoral trochlear osteotomy groove 12 is in the centering position with respect to the femur B, so as to perform the accurate osteotomy operation on the femoral trochlear along the femoral trochlear osteotomy groove 12 via a tool such as a sawblade.

An end of the cavity 10c adjacent to the fixing plate 20 has a restricting groove 10d. The restricting groove 10d can be used to restrict the rotation amplitude of the eccentric wheel 32 with the rotary knob 31, thereby restricting the relative displacement between the osteotomy plate 10 and the fixing plate 20, such that the stroke of the osteotomy plate 10 in the left-right direction with respect to the femur B can be adjusted appropriately, so as to prevent the latching tooth 20a and the latching tooth 20b from sliding out of the sliding groove 10a and the sliding groove 10b due to too much sliding of the osteotomy plate 10 in the left-right direction, or to prevent that the contact surfaces of the latching tooth 20a and the latching tooth 20b with the sliding groove 10a and the sliding groove 10b are too small to affects the fixation of the entire device. Specifically, when the eccentric wheel 32 moves to a limiting position that is required for the adjusting structure 30 to adjust the stroke of the osteotomy plate 10, the eccentric wheel 32 abuts against the end of the restricting groove 10d, such that the eccentric wheel 32 is restricted from rotating eccentrically.

It should be noted that, in some other embodiments, the restricting groove can be omitted, while the rotation amplitude of the eccentric wheel 32 is restricted by designing the size of the groove 22. Specifically, the groove 22 can be configured in a such way that when the eccentric wheel 32 moves to the limiting position that is required for the adjusting structure 30 to adjust the stoke of the osteotomy plate 10, the eccentric wheel 32 abuts against the end of the groove 22, and can no longer move eccentrically. Therefore, a better restricting effect can also be achieved on the rotation amplitude of the eccentric wheel 32.

In addition, the stroke of the osteotomy plate 10 that is driven by the eccentric wheel 32 to slide in the left-right direction with respect to the fixing plate 20 is also affected by the deviation of the eccentric wheel 32 from the rotation axis of the rotary knob 31 when the eccentric wheel 32 itself moves eccentrically. Specifically, the greater the deviation of the rotation track of the eccentric portion 322 of the eccentric wheel 32 from the rotation axis of the rotary knob 31, the greater the displacement of the osteotomy plate 10 that is driven by the eccentric wheel 32 to slide in the left-right direction with respect to the fixing plate 20, when the rotary knob 31 is rotated at the same angle. Therefore, the eccentric wheel 32 can be firstly selected, and then the eccentric wheel 32 is simulated to drive the osteotomy plate 10 to slide with respect to the fixing plate 20 to the limiting position of the preset stroke. At this time, the design of the size of the groove 22 can be completed by configuring an end position of the groove 22 to abut against the eccentric portion 322 of the eccentric wheel 32.

The width of the osteotomy plate 10 of the osteotomy device in the left-right direction corresponds to the width of the femur B to be osteotomized, such that when adjusting the position of the osteotomy plate 10 with respect to the femur B, the femur B can be used as the basis for determining the adjusted position, so as to quickly move the femoral trochlear osteotomy groove 12 on the osteotomy plate 10 to a position opposite to the femoral trochlear of the femur B.

Figure 4:
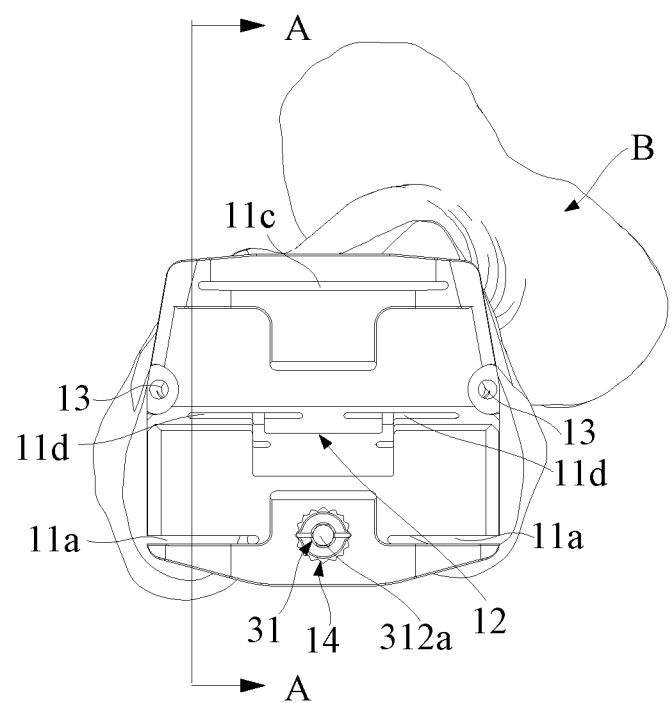
FIG. 4 is a schematic view of the osteotomy device being mounted to a femur according to an embodiment.

Referring to FIGS. 4 and 5, when using the osteotomy device to perform the surgical operation, firstly, the size of the femur B is measured via a size measuring device, and an external rotation angle thereof is determined. Then, an appropriate type of osteotomy device is selected according to the size of femur B. A side of the osteotomy device provided with the fixing plate 20 is attached to the distal end surface of the femur B, and the fixing nails 21 on the fixing plate 20 are used to perform a preliminary fixing of the osteotomy device. The amount of the adjustment in the left-right direction is determined by the relative positions of both sides of the osteotomy plate 10 and the internal and external sides of the femur B. Then, the rotary knob 31 is adjusted by using a hexagon wrench or similar device, so as to drive the eccentric wheel 32 to rotate. When the eccentric wheel 32 rotates, the osteotomy plate 10 is driven to move to an appropriate position in the left-right direction. After the adjustment is completed, oblique nails are driven into the femur B via the nail holes 13 on the osteotomy plate 10, so as to fix the osteotomy plate 10, such that the osteotomy plate 10 is firmly fixed by the fixing nails 21 and the oblique nails, thereby avoiding osteotomy errors caused by loosening. Then, the four-sided osteotomy is performed sequentially along the four femoral osteotomy grooves 11a, 11b, 11c, and 11d by using the sawblade. After the four-sided osteotomy is completed, the femoral trochlear osteotomy can be performed along the femoral trochlear osteotomy groove 12 by the sawblade, or treated by a matching U-shaped bone chisel. After the osteotomy operation is completed, the oblique nails are firstly taken out, and then the osteotomy plate 10 is taken out via the T-shaped groove 15 on the osteotomy plate 10 by an extraction tool such as sliding hammer, so as to perform a reset operation on the subsequent femoral B provisional.

Figure 6:
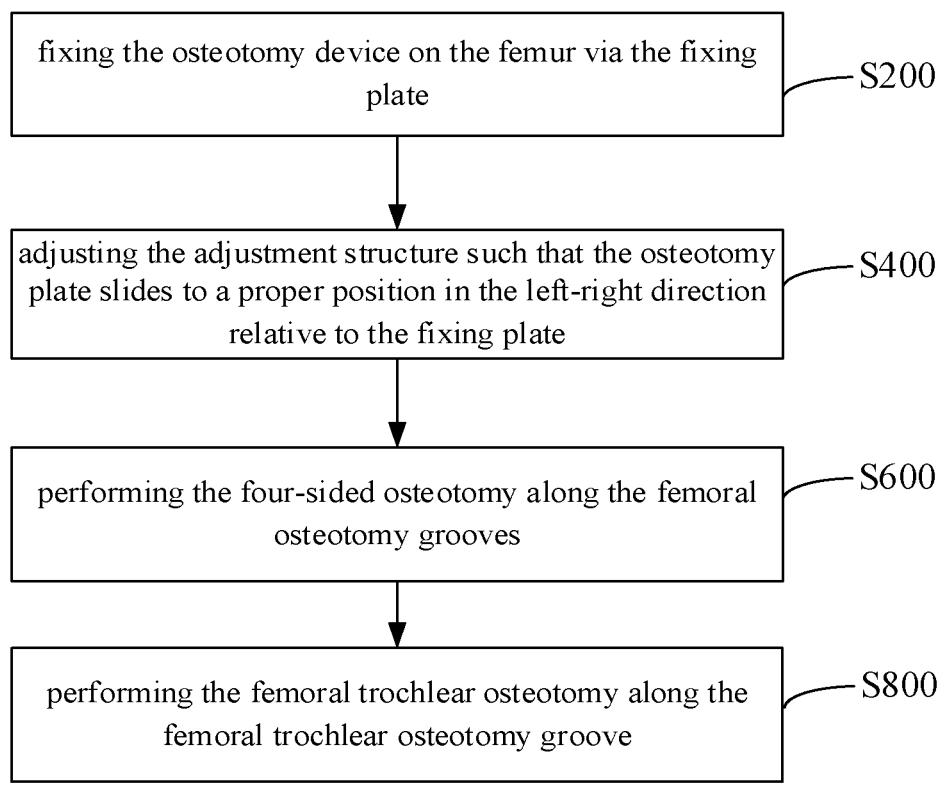
FIG. 6 is a flowchart of a method for operating the osteotomy device according to an embodiment.

Referring to FIG. 6, an embodiment of a method for operating an osteotomy device is illustrated. In this embodiment, the osteotomy device is an osteotomy device as described in any one of the embodiments. The osteotomy device is mounted by the method, and thus the surgical operation is performed. Specifically, the method includes the following steps.

In step S200, the osteotomy device is fixed on the femur via the fixing plate.

In step S400, the adjusting structure is adjusted, such that the osteotomy plate slides to an appropriate position in the left-right direction with respect to the fixing plate.

In step S600, the four-sided osteotomy is performed along the femoral osteotomy grooves.

In step S800, the femoral trochlear osteotomy is performed along the femoral trochlear osteotomy groove.

The steps have been set forth in detail in the above descriptions, and the redundant description thereof will not be made herein.

It should be noted that, it should be understood that although the steps in the flowchart in FIG. 6 are shown in sequence according to the arrows, the steps are not necessarily performed in the sequence indicated by the arrows. Unless clearly stated in the context, performing these steps is not strictly limited in sequence, and these steps can be performed in other sequences. Moreover, at least some of the steps in FIG. 6 may include multiple sub-steps or multiple stages. These sub-steps or stages are not necessarily performed at the same time, but may be performed at different times. The performing order of these sub-steps or stages also does not have to be performed in sequence, but may be performed in turn or alternately with at least some of other steps or sub-steps or stages of other steps.

Each technical features of the above embodiments can be arbitrarily combined. For simplifying the description, all possible combinations of each technical features in the embodiments are not described. However, as long as there is no contradiction in the combination of these technical features, they should be fallen within the scope of this description.

Only several embodiments of the present disclosure are illustrated in the embodiments, and descriptions thereof are more specific and detailed, but they should not be construed as limiting the scope of the disclosure. It should be noted that, for those skilled in the art, several modifications and improvements can be made without departing from the concept of the present disclosure, which all fall within the protection scope of the present disclosure. Therefore, the protection scope of the disclosure shall be subject to the appended claims.

What is claimed is:

1. An osteotomy device, comprising:
   a fixing plate;
   an osteotomy plate configured to be mounted on a femur via the fixing plate; and
   an adjusting structure, both ends of the adjusting structure being configured to be connected to the fixing plate and the osteotomy plate respectively, the osteotomy plate being capable of sliding in a left-right direction with respect to the fixing plate via the adjusting structure;
   wherein the osteotomy plate has a femoral osteotomy groove to perform a four-sided osteotomy and a femoral trochlear osteotomy groove to perform a femoral trochlear osteotomy.

2. The osteotomy device according to claim 1, wherein upper and lower ends of the fixing plate are each provided with a latching tooth, a surface of the osteotomy plate facing the fixing plate is provided with a sliding groove, the latching tooth is slidably engaged in the sliding groove, the latching tooth and the sliding groove are capable of sliding with respect to each other in a horizontal direction.

3. The osteotomy device according to claim 1 or 2, wherein the adjusting structure comprises:
   an eccentric wheel connected to the fixing plate; and
   a rotary knob connected to the eccentric wheel and rotatably connected to the osteotomy plate;
   wherein when the rotary knob rotates, the eccentric wheel moves eccentrically with respect to the rotary knob, so as to enable the osteotomy plate to slide in the left-right direction with respect to the fixing plate.

4. The osteotomy device according to claim 3, wherein the eccentric wheel comprises:
   a rotary connecting portion connected to the rotary knob; and
   an eccentric portion deviated from a rotation axis of the rotary knob.

5. The osteotomy device according to claim 4, wherein the fixing plate is provided with a groove, the eccentric portion is embedded in the groove; wherein when the eccentric wheel rotates along with the rotary knob, the eccentric portion is capable of sliding in an up-down direction along the groove.

6. The osteotomy device according to claim 5, wherein the osteotomy plate is provided with a cavity penetrating through the osteotomy plate, the cavity and the groove are communicated to form a hollow cavity; the rotary knob is located in the cavity; wherein when the eccentric wheel rotates, the rotary knob abuts against a sidewall of the cavity to drive the osteotomy plate to slide in the left-right direction.

7. The osteotomy device according to claim 3, wherein the eccentric wheel and the rotary knob are capable of moving relatively in an axial direction, and the eccentric wheel is radially restricted to the rotary knob, an elastic compression member is provided between the eccentric wheel and the rotary knob, both ends of the elastic compression member elastically abut against the eccentric wheel and the rotary knob respectively.

8. The osteotomy device according to claim 6, wherein the rotary knob has a stepped shape, one end of the rotary knob adjacent to the eccentric wheel has an inserting portion, and the other end thereof has a toothed disc, the rotary connecting portion of the eccentric wheel is provided with an inserting slot matching with the inserting portion, an end of the cavity away from the fixing plate has a toothed opening, the toothed disc is capable of being embedded in or removed from the toothed opening along the rotation axis of the rotary knob, when the toothed disc is embedded in the toothed opening, the toothed opening restricts a rotational movement of the rotary knob with respect to the osteotomy plate.

9. The osteotomy device according to claim 5, wherein a bottom portion of the groove is provided with a through hole penetrating through the fixing plate.

10. The osteotomy device according to claim 6, wherein an end of the cavity adjacent to the fixing plate has a restricting groove, when the eccentric wheel moves to a limiting position that is required for the adjusting structure to adjust a stroke of the osteotomy plate, the eccentric wheel abuts against an end of the restricting groove, such that the eccentric wheel is restricted from rotating eccentrically.

11. The osteotomy device according to claim 1, wherein a side of the fixing plate away from the osteotomy plate is provided with a fixing nail configured to mount the fixing plate on the femur.

* * * * *